United States Patent
Izuchukwu et al.

(10) Patent No.: US 6,412,484 B1
(45) Date of Patent: Jul. 2, 2002

(54) FLUID CONTROL VALVE FOR PRESSURE VESSEL

(75) Inventors: John I. Izuchukwu, Wildwood; Stan A. Sanders; Richard Scott Remes, both of Chesterfield, all of MO (US)

(73) Assignee: Mallinckrodt Inc., St. Louis, MO (US)

( * ) Notice: Subject to any disclaimer, the term of this patent is extended or adjusted under 35 U.S.C. 154(b) by 52 days.

(21) Appl. No.: 09/592,664

(22) Filed: Jun. 13, 2000

(51) Int. Cl.[7] .................................................. A62B 7/00
(52) U.S. Cl. ........................... 128/205.22; 128/202.19; 285/256
(58) Field of Search ........................ 137/68.19, 68.23, 137/71; 285/138, 196, 216, 238, 239, 256; 128/202.11, 202.18, 202.19, 205.13, 205.22

(56) References Cited

U.S. PATENT DOCUMENTS

| | | | |
|---|---|---|---|
| 601,591 A | * 3/1898 | Sherman .................... 285/256 |
| 724,129 A | 3/1903 | Schrader |
| 771,801 A | 10/1904 | Andrew |
| 1,288,857 A | 12/1918 | Farr ....................... 128/205.22 |
| 1,348,708 A | 8/1920 | Garland |
| 1,410,405 A | * 3/1922 | Johnson ..................... 285/245 |
| 1,588,606 A | 6/1926 | Oden |
| 1,745,785 A | 2/1930 | Deming |
| 1,778,244 A | 10/1930 | Cadden |
| 1,786,489 A | * 12/1930 | Hopkins ..................... 285/256 |
| 1,901,088 A | * 3/1933 | Dick .......................... 285/256 |
| 2,319,024 A | 5/1943 | Wehringer |
| 2,376,353 A | 5/1945 | Grant, Jr. et al. |
| 2,380,372 A | 7/1945 | Alderfer ..................... 244/148 |
| 2,430,921 A | 11/1947 | Edelmann |
| 2,524,052 A | * 10/1950 | Grant, Jr. ................... 137/68.23 |
| 2,531,700 A | * 11/1950 | Porter ........................ 285/256 |
| 2,540,113 A | * 2/1951 | Hartley et al. .............. 285/245 |
| 2,764,430 A | 9/1956 | Roberts |
| 2,771,069 A | 11/1956 | Baron |
| 2,814,291 A | 11/1957 | Holmes |
| 2,829,671 A | 4/1958 | Ernst et al. |
| 2,861,569 A | 11/1958 | Emerson |
| 3,185,500 A | 5/1965 | Luther |
| 3,338,238 A | 8/1967 | Warncke ................. 128/142.2 |
| 3,432,060 A | 3/1969 | Cowley ......................... 220/3 |
| 3,491,752 A | 1/1970 | Cowley ..................... 128/147 |
| 3,729,002 A | 4/1973 | Miller |
| 4,060,079 A | 11/1977 | Reinhold, Jr. |
| 4,090,509 A | 5/1978 | Smith ..................... 128/142.5 |
| 4,181,993 A | 1/1980 | McDaniel ..................... 9/329 |
| 4,253,454 A | 3/1981 | Warncke ................ 128/202.26 |
| 4,584,996 A | 4/1986 | Blum |
| 4,612,928 A | 9/1986 | Tiep et al. |
| 4,665,943 A | 5/1987 | Medvick et al. ......... 137/543.17 |
| 4,736,969 A | 4/1988 | Fouts |
| 4,739,913 A | 4/1988 | Moore |
| 4,744,356 A | 5/1988 | Greenwood |

(List continued on next page.)

FOREIGN PATENT DOCUMENTS

| | | |
|---|---|---|
| DE | 971689 | 3/1959 |
| DE | 2644806 | 4/1978 |
| FR | 1037477 | 9/1953 |
| WO | WO 97/11734 | 4/1997 |

Primary Examiner—Aaron J. Lewis
(74) Attorney, Agent, or Firm—Rothwell, Figg, Ernst & Manbeck

(57) ABSTRACT

A fluid transfer control valve is connected to a pressure vessel formed from a plurality of hollow, polymeric chambers interconnected by polymeric conduit sections disposed between adjacent ones of the chambers. The valve includes a valve body and a pressure relief mechanism attached to the body. The pressure relief mechanism is operative to release pressure from the pressure vessel when the pressure within the vessel exceeds a predetermined maximum pressure. In a preferred embodiment, the relief mechanism comprises a rupture disk. The pressure relief valve may also include a filter element disposed along a fluid flow path defined within the valve body and/or a restrictive flow path for reducing the pressure of fluid flowing through the valve body.

22 Claims, 13 Drawing Sheets

U.S. PATENT DOCUMENTS

| | | | |
|---|---|---|---|
| 4,800,923 A | 1/1989 | Bartos | 137/613 |
| 4,932,403 A | 6/1990 | Scholley | 128/205.22 |
| 4,964,404 A | 10/1990 | Stone | |
| 4,964,405 A | 10/1990 | Arnoth | |
| 4,989,599 A | 2/1991 | Carter | 128/207.18 |
| 4,991,876 A * | 2/1991 | Mulvey | 285/256 |
| 5,036,845 A | 8/1991 | Scholley | 128/205.22 |
| 5,099,836 A | 3/1992 | Rowland et al. | |
| 5,127,399 A | 7/1992 | Scholley | 128/205.22 |
| 5,323,953 A | 6/1994 | Adderley et al. | 228/157 |
| 5,370,113 A | 12/1994 | Parsons | |
| 5,400,934 A | 3/1995 | Ducros | |
| 5,435,305 A | 7/1995 | Rankin, Sr. | 128/205.22 |
| 5,494,469 A | 2/1996 | Heath et al. | 441/118 |
| 5,503,143 A | 4/1996 | Marion et al. | |
| 5,517,984 A | 5/1996 | Sanders | 128/205.22 |
| 5,529,061 A | 6/1996 | Sanders | 128/205.22 |
| 5,529,096 A * | 6/1996 | Rowe, Jr. et al. | 128/205.22 |
| 5,582,164 A | 12/1996 | Sanders | 128/205.22 |
| 5,632,268 A | 5/1997 | Ellis et al. | |
| 5,830,400 A | 11/1998 | Huvey et al. | 264/254 |
| 5,839,383 A | 11/1998 | Stenning et al. | 114/72 |
| 5,975,081 A | 11/1999 | Hood et al. | |
| 6,003,460 A | 12/1999 | Stenning et al. | 114/72 |
| 6,047,860 A | 4/2000 | Sanders | 222/3 |
| 6,187,182 B1 | 2/2001 | Reynolds et al. | |
| 6,230,737 B1 | 5/2001 | Notaro et al. | |
| 6,240,951 B1 | 6/2001 | Yori | |

\* cited by examiner

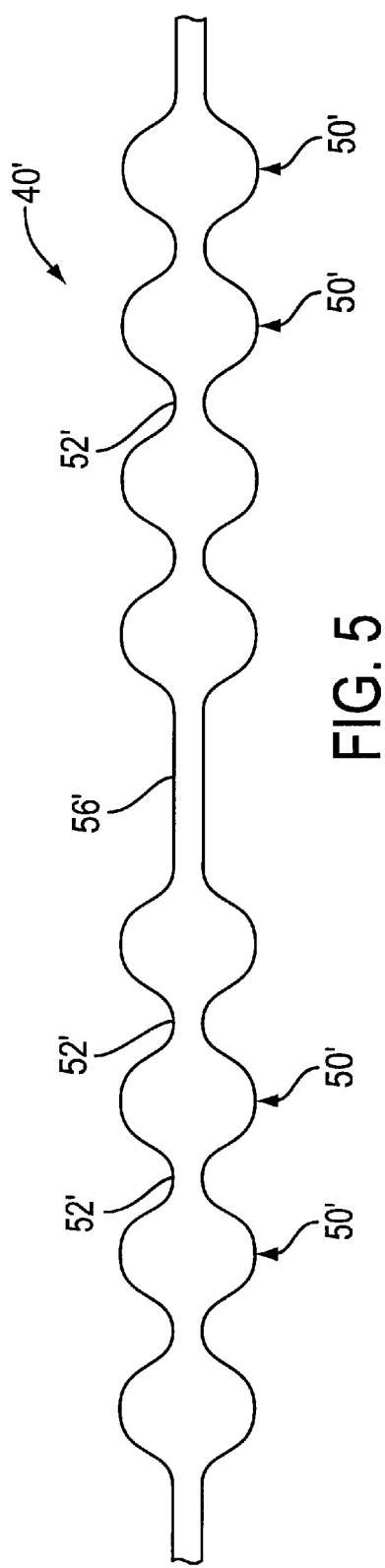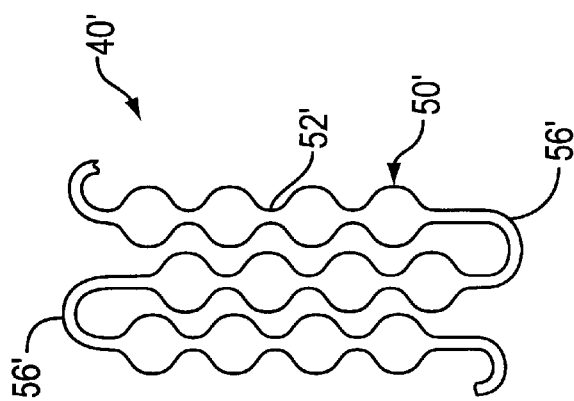

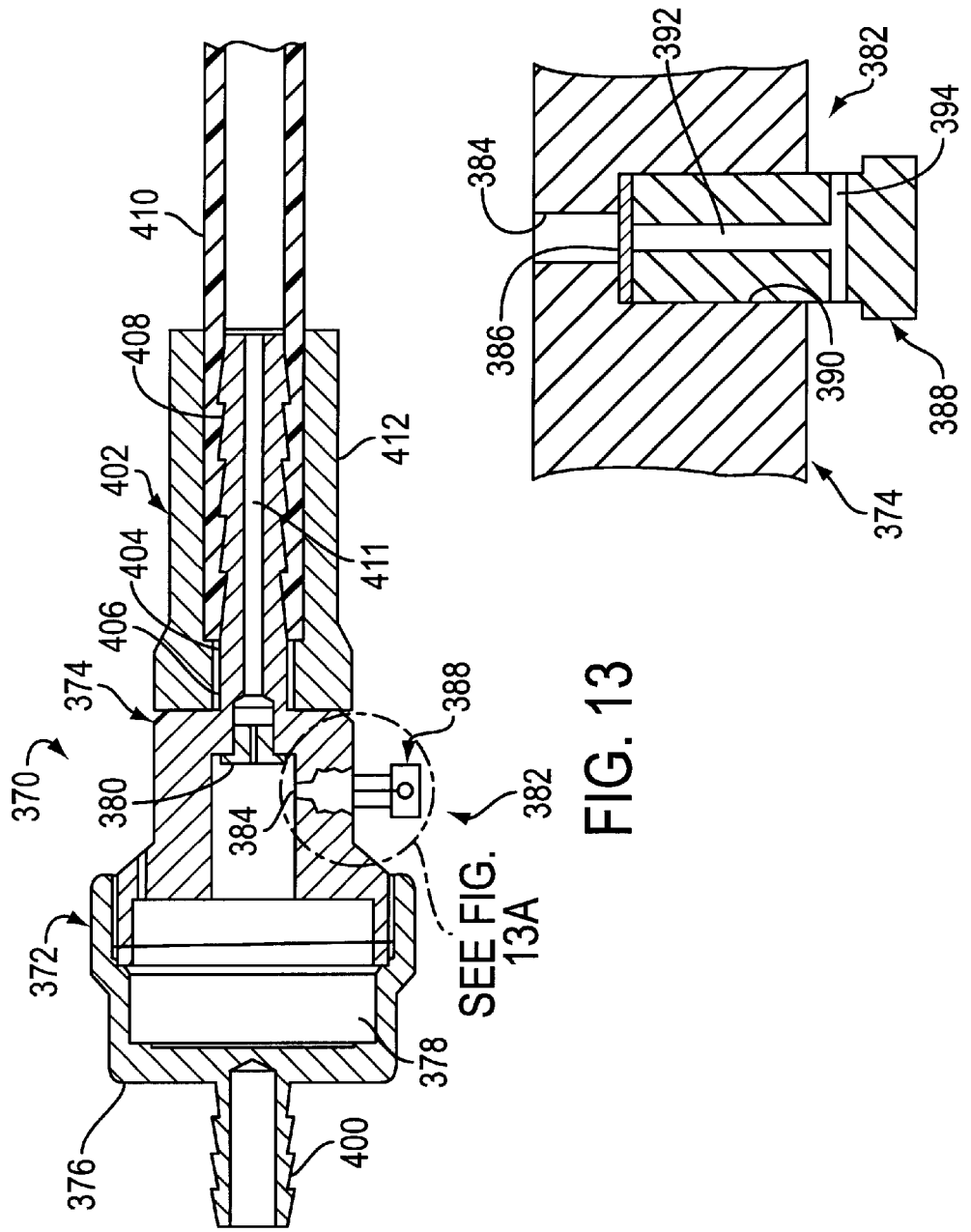

FLUID CONTROL VALVE FOR PRESSURE VESSEL

FIELD OF THE INVENTION

The present invention is directed to a container system for pressurized fluids including a pressure vessel that is lightweight and compact and a fluid control valve for regulating fluid flow into and/or out of the pressure vessel.

BACKGROUND OF THE INVENTION

There are many applications for a portable supply of fluid under pressure. For example, SCUBA divers and firefighters use portable, pressurized oxygen supplies. Commercial aircraft employ emergency oxygen delivery systems that are used during sudden and unexpected cabin depressurization. Military aircraft typically require supplemental oxygen supply systems as well. Such systems are supplied by portable pressurized canisters. In the medical field, gas delivery systems are provided to administer medicinal gas, such as oxygen, to a patient undergoing respiratory therapy. Supplemental oxygen delivery systems are used by patients that benefit from receiving and breathing oxygen from an oxygen supply source to supplement atmospheric oxygen breathed by the patient. For such uses, a compact, portable supplemental oxygen delivery system is useful in a wide variety of contexts, including hospital, home care, and ambulatory settings.

High-pressure supplemental oxygen delivery systems typically include a cylinder or tank containing oxygen gas at a pressure of up to 3,000 psi. A pressure regulator is used in a high-pressure oxygen delivery system to "step down" the pressure of oxygen gas to a lower pressure (e.g., 20 to 50 psi) suitable for use in an oxygen delivery apparatus used by a person breathing the supplemental oxygen.

In supplemental oxygen delivery systems, and in other applications employing portable supplies of pressurized gas, containers used for the storage and use of compressed fluids, and particularly gases, generally take the form of cylindrical metal bottles that may be wound with reinforcing materials to withstand high fluid pressures. Such storage containers are expensive to manufacture, inherently heavy, bulky, inflexible, and prone to violent and explosive fragmentation upon rupture.

Container systems made from lightweight synthetic materials have been proposed. Scholley, in U.S. Pat. Nos. 4,932,403; 5,036,845; and 5,127,399, describes a flexible and portable container for compressed gases which comprises a series of elongated, substantially cylindrical chambers arranged in a parallel configuration and interconnected by narrow, bent conduits and attached to the back of a vest that can be worn by a person. The container includes a liner, which may be formed of a synthetic material such as nylon, polyethylene, polypropylene, polyurethane, tetrafluoroethylene, or polyester. The liner is covered with a high-strength reinforcing fiber, such as a high-strength braid or winding of a reinforcing material such as Kevlar® aramid fiber, and a protective coating of a material, such as polyurethane, covers the reinforcing fiber. The design described in the Scholley patents suffers a number of shortcomings which makes it impractical for use as a container for fluids stored at the pressure levels typically seen in portable fluid delivery systems such as SCUBA gear, firefighter's oxygen systems, emergency oxygen systems, and medicinal oxygen systems. The elongated, generally cylindrical shape of the separate storage chambers does not provide an effective structure for containing highly-pressurized fluids. Moreover, the relatively large volume of the storage sections creates an unsafe system subject to possible violent rupture due to the kinetic energy of the relatively large volume of pressurized fluid stored in each chamber.

SUMMARY OF THE INVENTION

In accordance with aspects of the present invention, a container system for pressurized fluids comprises a pressure vessel with a fluid flow control valve attached thereto. The pressure vessel comprises a plurality of hollow chambers formed from a polymeric material interconnected by polymeric conduit sections disposed between consecutive ones of the hollow chambers. The fluid transfer control valve controls the flow of fluid with respect to the interior of the pressure vessel defined by the interiors of the hollow chambers and the conduit sections. The fluid transfer control valve comprises a valve body having a fluid chamber formed therein. At least a portion of the chamber is in fluid communication with the interior of said pressure vessel. The valve further includes a pressure relief mechanism coupled to the fluid chamber and constructed and arranged to permit fluid to flow out of the pressure vessel when the fluid within the pressure vessel exceeds a prescribed threshold level to thereby reduce pressure within the pressure vessel.

The fluid flow control valve may also include a filter element disposed along a fluid flow path formed in the valve body. Alternatively, or in addition, a portion of the flow path may be formed as a restrictive flow path to reduce the pressure of fluid flowing through the flow path.

Other objects, features, and characteristics of the present invention will become apparent upon consideration of the following description and the appended claims with reference to the accompanying drawings, all of which form a part of the specification, and wherein like reference numerals designate corresponding parts in the various figures.

DESCRIPTION OF THE DRAWINGS

FIG. 5 is a side elevational view of an alternative embodiment of the container system of the present invention.

FIG. 5A is a partial view of the container system of FIG. 5 arranged in a sinuous configuration.

FIG. 13 is a partial view in longitudinal section of a preferred outlet valve/regulator for incorporation into the pressure pack employing the container system of the present invention.

FIG. 13A is an enlarged view of a portion of FIG. 13 within circle "A".

DETAILED DESCRIPTION OF THE INVENTION

With reference to the figures, exemplary embodiments of the invention will now be described. These embodiments illustrate principles of the invention and should not be construed as limiting the scope of the invention.

Figure 1:
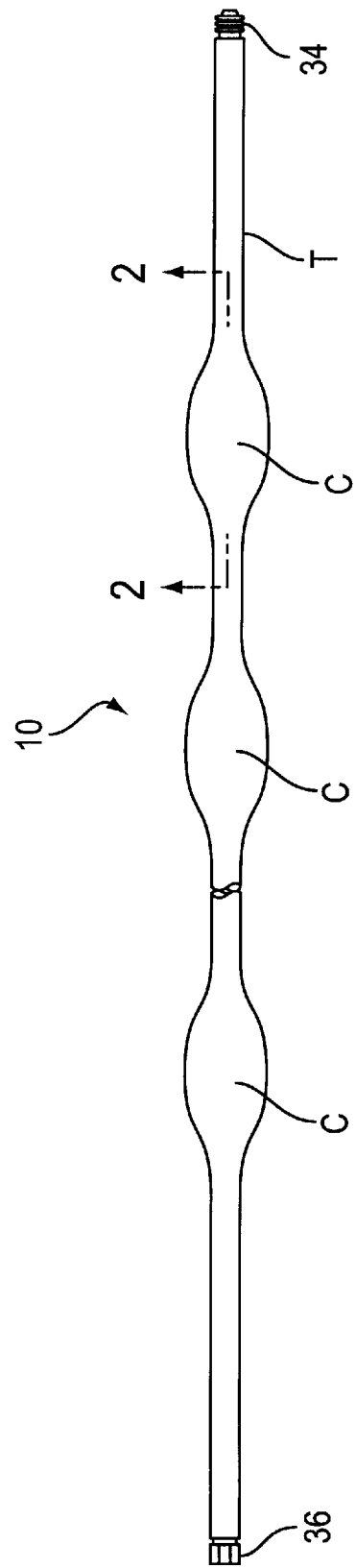
FIG. 1 is a broken side elevational view of a plurality of aligned, rigid, generally ellipsoidal chambers interconnected by a tubular core.
Figure 2:
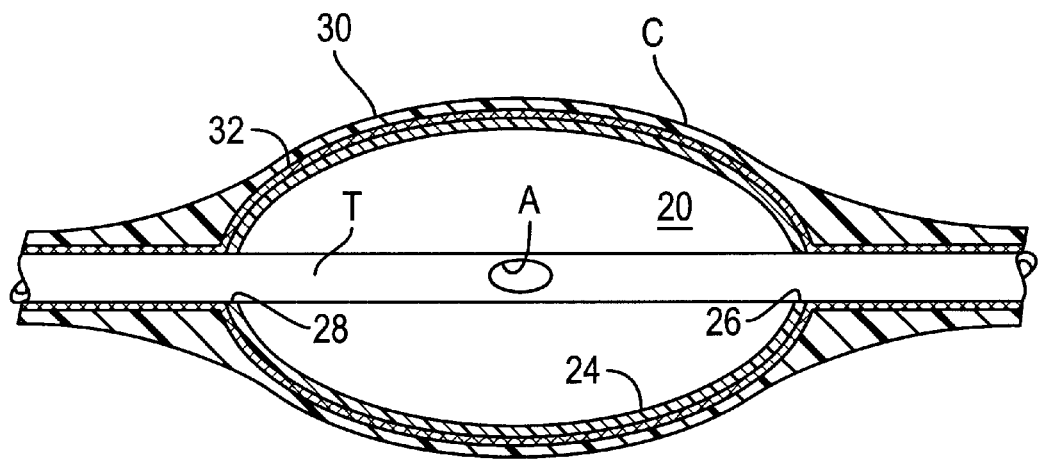
FIG. 2 is an enlarged horizontal sectional view taken along the line 2—2 in FIG. 1.

As shown in FIGS. 1 and 2, U.S. Pat. No. 6,047,860 (the disclosure of which is hereby incorporated by reference) to Sanders, an inventor of the present invention, discloses a container system 10 for pressurized fluids including a plurality of form-retaining, generally ellipsoidal chambers C interconnected by a tubular core T. The tubular core extends through each of the plurality of chambers and is sealingly secured to each chamber. A plurality of longitudinally-spaced apertures A are formed along the length of the tubular core, one such aperture being disposed in the interior space 20 of each of the interconnected chambers so as to permit infusion of fluid to the interior space 20 during filling and effusion of the fluid from the interior space 20 during fluid delivery or transfer to another container. The apertures are sized so as to control the rate of evacuation of pressurized fluid from the chambers. Accordingly, a low fluid evacuation rate can be achieved so as to avoid a large and potentially dangerous burst of kinetic energy should one or more of the chambers be punctured (i.e., penetrated by an outside force) or rupture.

The size of the apertures A will depend upon various parameters, such as the volume and viscosity of fluid being contained, the anticipated pressure range, and the desired flow rate. In general, smaller diameters will be selected for gasses as opposed to liquids. Thus, the aperture size may generally vary from about 0.010 to 0.125 inches. Although only a single aperture A is shown in FIG. 2, more than one aperture A can be formed in the tube T within the interior space 20 of the shell 24. In addition, each aperture A can be formed in only one side of the tube T, or the aperture A may extend through the tube T.

Referring to FIG. 2, each chamber C includes a generally ellipsoidal shell 24 molded of a suitable synthetic plastic material and having open front and rear ends 26 and 28. The diameters of the holes 26 and 28 are dimensioned so as to snugly receive the outside diameter of the tubular core T. The tubular core T is attached to the shells 24 so as to form a fluid tight seal therebetween. The tubular core T is preferably bonded to the shells 24 by means of light, thermal, or ultrasonic energy, including techniques such as, ultrasonic welding, radio frequency energy, vulcanization, or other thermal processes capable of achieving seamless circumferential welding. The shells 24 may be bonded to the tubular core T by suitable ultraviolet light-curable adhesives, such as 3311 and 3341 Light Cure Acrylic Adhesives available from Loctite Corporation, having authorized distributors throughout the world. The exterior of the shells 24 and the increments of tubular core T between such shells are pressure wrapped with suitable pressure resistant reinforcing filaments 30 to resist bursting of the shells and tubular core. A protective synthetic plastic coating 32 is applied to the exterior of the filament wrapped shells and tubular core T.

More particularly, the shells 24 may be either roto molded, blow molded, or injection molded of a synthetic plastic material such as TEFLON or fluorinated ethylene propylene. Preferably, the tubular core T will be formed of the same material. The pressure resistant filaments 30 may be made of a carbon fiber, Kevlar® or Nylon. The protective coating 32 may be made of urethane to protect the chambers and tubular core against abrasions, UV rays, moisture, or thermal elements. The assembly of a plurality of generally ellipsoidal chambers C and their supporting tubular core T can be made in continuous strands of desired length. In the context of the present disclosure, unless stated otherwise, the term "strand" will refer to a discrete length of interconnected chambers.

Figure 2A:
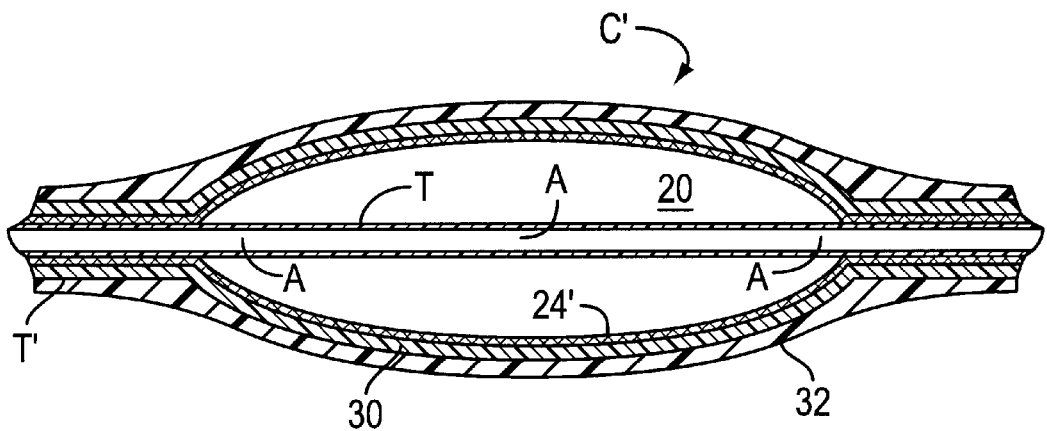
FIG. 2A is an enlarged horizontal sectional view taken along the line 2—2 in FIG. 1 showing an alternate embodiment.

As shown in FIG. 2A, the tube T can be co-formed, such as by co-extrusion, along with shells 24' and tubular portions T' integrally formed with the shells 24' and which directly overlie the tube T between adjacent shells 24'. Furthermore, as also shown in FIG. 2A, more than one aperture A may be formed in the tube T within the interior 20 of the shell 24'. The co-formed assembly comprised of the shells 24', tubular portions T', and tube T can be wrapped with a layer of reinforcing filaments 30 and covered with a protective coating 32 as described above.

The inlet or front end of the tubular core T may be provided with a suitable threaded male fitting 34. The discharge or rear end of a tubular core T may be provided with a threaded female fitting 36. Such male and female fittings provide a pressure-type connection between contiguous strands of assemblies of chambers C interconnected by tubular cores T and provide a mechanism by which other components, such as gauges and valves, can be attached to the interconnected chambers. A suitable mechanism for attaching fittings, such as fittings 34 and 36, is described below.

Figure 3:
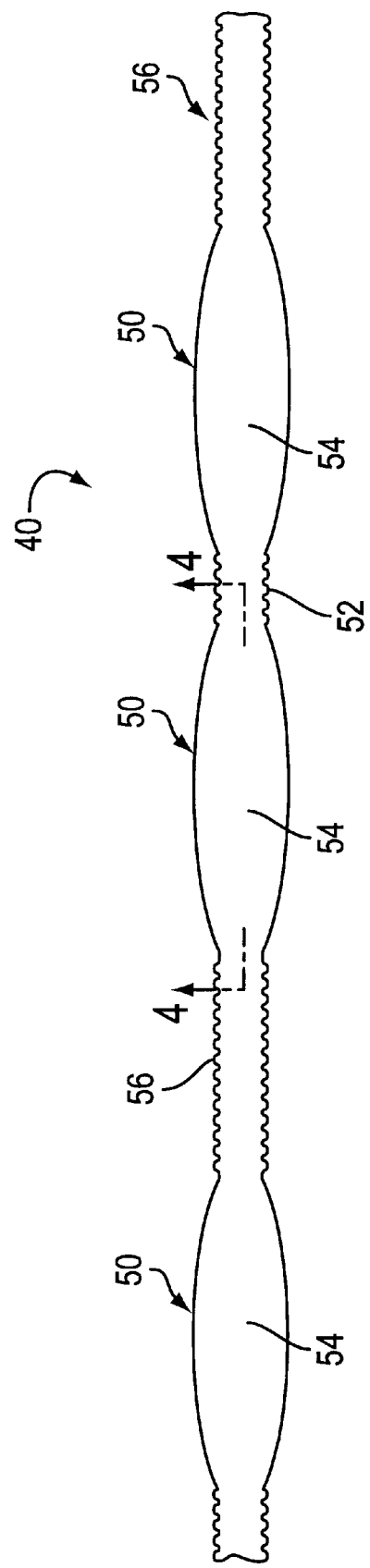
FIG. 3 is a side elevational view of a portion of a container system of the present invention.

A portion of an alternate pressure vessel is designated generally by reference number 40 in FIG. 3. The pressure vessel 40 includes a plurality of fluid storage chambers 50 having a preferred ellipsoidal shape and having hollow interiors 54. The individual chambers 50 are pneumatically interconnected with each other by connecting conduit sections 52 and 56 disposed between adjacent pairs of the chambers 50. Conduit sections 56 are generally longer than the conduit sections 52. The purpose of the differing lengths of the conduit sections 52 and 56 will be described in more detail below.

Figure 4:
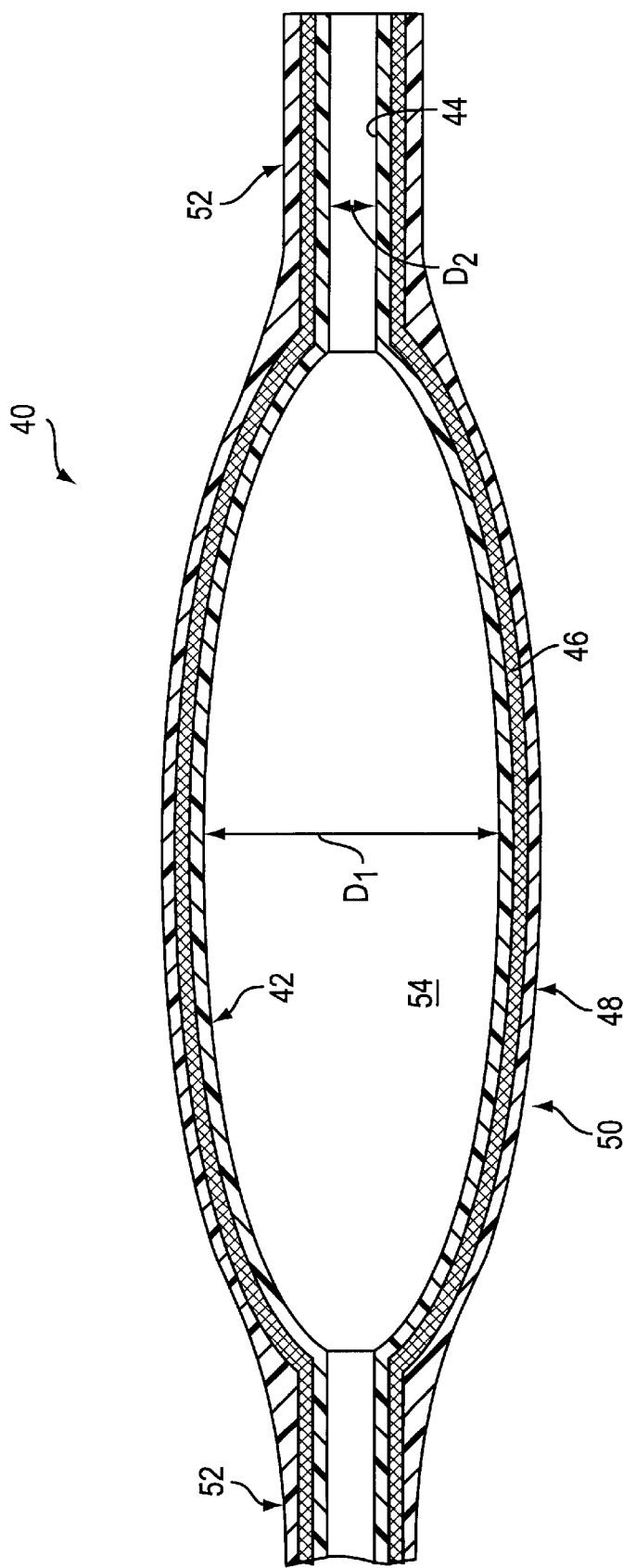
FIG. 4 is a partial longitudinal sectional view along line 4—4 in FIG. 3.

FIG. 4 shows an enlarged longitudinal section of a single hollow chamber 50 and portions of adjacent conduit sections 52 of the pressure vessel 40. The pressure vessel 40 preferably has a layered construction including polymeric hollow shells 42 with polymeric connecting conduits 44 extended from opposed open ends of the shells 42. The polymeric shells 42 and the polymeric connecting conduits 44 are preferably formed from a synthetic plastic material such as Teflon or fluorinated ethylene propylene and may be formed by any of a number of known plastic-forming techniques such as extrusion, roto molding, chain blow molding, or injection molding.

Materials used for forming the shells 42 and connecting conduits 44 are preferably moldable and exhibit high tensile strength and tear resistance. Most preferably, the polymeric hollow shells 42 and the polymeric connecting conduits 44 are formed from a thermoplastic polyurethane elastomer manufactured by Dow Plastics under the name Pellethane® 2363-90AE, a thermoplastic polyurethane elastomer manufactured by the Bayer Corporation, Plastics Division under the name Texing® 5286, a flexible polyester manufactured by Dupont under the name Hytrel®, or polyvinyl chloride from Teknor Apex.

In a preferred configuration, the volume of the hollow interior 54 of each chamber 50 is within a range of capacities configurable for different applications, with a most preferred volume of about thirty (30) milliliters. It is not necessary that each chamber have the same dimensions or have the same capacity. It has been determined that a pressure vessel 40 having a construction as will be described below will undergo a volume expansion of 7–10% when subjected to an internal pressure of 2000 psi. In a preferred configuration, the polymeric shells 42 each have a longitudinal length of about 3.0–3.5 inches, with a most preferred length of 3.250–3.330 inches, and a maximum outside diameter of about 0.800 to 1.200 inches, with a most preferred diameter of 0.095–1.050 inches. The conduits 44 have an inside diameter $D_2$ preferably ranging from 0.125–0.300 inches with a most preferred range of about 0.175–0.250 inches. The hollow shells 42 have a typical wall thickness ranging from 0.03 to 0.05 inches with a most preferred typical thickness of about 0.04 inches. The connecting conduits 44 have a wall thickness ranging from 0.03 to 0.10 inches and preferably have a typical wall thickness of about 0.040 inches, but, due to the differing amounts of expansion experienced in the hollow shells 42 and the conduits 44 during a blow molding forming process, the conduits 44 may actually have a typical wall thickness of about 0.088 inches.

The exterior surface of the polymeric hollow shells 42 and the polymeric connecting conduits 44 is preferably wrapped with a suitable reinforcing filament fiber 46. Filament layer 46 may be either a winding or a braid (preferably a triaxial braid pattern having a nominal braid angle of 75 degrees) and is preferably a high-strength aramid fiber material such as Kevlar® (preferably 1420 denier fibers), carbon fibers, or nylon, with Kevlar® being most preferred. Other potentially suitable filament fiber material may include thin metal wire, glass, polyester, or graphite. The Kevlar winding layer has a preferred thickness of about 0.035 to 0.055 inches, with a thickness of about 0.045 inches being most preferred.

A protective coating 48 may be applied over the layer of filament fiber 46. The protective coating 48 protects the shells 42, conduits 44, and the filament fiber 46 from abrasions, UV rays, thermal elements, or moisture. Protective coating 32 is preferably a sprayed-on synthetic plastic coating. Suitable materials include polyvinyl chloride and polyurethane. The protective coating 32 may be applied to the entire pressure vessel 40, or only to more vulnerable portions thereof. Alternatively, the protective coating 32 could be dispensed with altogether if the pressure vessel 40 is encased in a protective, moisture-impervious housing.

The inside diameter $D_1$ of the hollow shell 42 is preferably much greater than the inside diameter $D_2$ of the conduit section 44, thereby defining a relatively discreet storage chamber within the hollow interior 54 of each polymeric shell 42. This serves as a mechanism for reducing the kinetic energy released upon the rupturing of one of the chambers 50 of the pressure vessel 40. That is, if one of the chambers 50 should rupture, the volume of pressurized fluid within that particular chamber would escape immediately. Pressurized fluid in the remaining chambers would also move toward the rupture, but the kinetic energy of the escape of the fluid in the remaining chambers would be regulated by the relatively narrow conduit sections 44 through which the fluid must flow on its way to the ruptured chamber. Accordingly, immediate release of the entire content of the pressure vessel is avoided.

An alternate pressure vessel 40' is shown in FIGS. 5 and 5A. Pressure vessel 40' includes a plurality of hollow chambers 50' having a generally spherical shape connected by conduit sections 52' and 56'. As shown in FIG. 5A, one particular configuration of the pressure vessel 40' is to bend it back-and-forth upon itself in a sinuous fashion. The pressure vessel 40' is bent at the elongated conduit sections 56', which are elongated relative to the conduit sections 52' so that they can be bent without kinking or without adjacent hollow chambers 50' interfering with each other. Accordingly, the length of the conduit sections 56' can be defined so as to permit the pressure vessel to be bent thereat without kinking and without adjacent hollow chambers 50' interfering with each other. In general, a connecting conduit section 56' of sufficient length can be provided by omitting a chamber 50' in the interconnected series of chambers 50'. The length of a long conduit section 56', however, need not necessarily be as long as the length of a single chamber 50'.

Both ellipsoidal and the spherical chambers are preferred, because such shapes are better suited than other shapes, such as cylinders, to withstand high internal pressures. Spherical chambers 50' are not, however, as preferable as the generally ellipsoidal chambers 50 of FIGS. 3 and 4, because, the more rounded a surface is, the more difficult it is to apply a consistent winding of reinforcing filament fiber. Filament fibers, being applied with axial tension, are more prone to slipping on highly rounded, convex surfaces.

A portable pressure pack 60 employing a pressure vessel 40 as described above is shown in FIG. 6. Note that the pressure pack 60 includes a pressure vessel 40 having generally ellipsoidal hollow chambers 50. It should be understood, however, that a pressure vessel 40 of a type having generally spherical hollow chambers as shown in FIGS. 5 and 5A could be employed in the pressure pack 60 as well. The pressure vessel 40 is arranged as a continuous, serial strand 58 of interconnected chambers 50 bent back-and-forth upon itself in a sinuous fashion with all of the chambers lying generally in a common plane. In general, the axial arrangement of any strand of interconnected chambers can be an orientation in any angle in X-Y-Z Cartesian space. Note again, in FIG. 6, that elongated conduit sections 56 are provided. Sections 56 are substantially longer than conduit sections 52 and are provided to permit the pressure vessel 40 to be bent back upon itself without kinking the conduit section 56 or without adjacent chambers 50 interfering with one another. Again, an interconnecting conduit 56 of sufficient length for bending can be provided by omitting a chamber 50 from the strand 58 of interconnected chambers.

The pressure vessel 40 is encased in a protective housing 62. Housing 62 may have a handle, such as an opening 64, provided therein.

A fluid transfer control system 76 is pneumatically connected to the pressure vessel 40 and is operable to control transfer of fluid under pressure into or out of the pressure vessel 40. In the embodiment illustrated in FIG. 6, the fluid transfer control system includes a one-way inlet valve 70 (also known as a fill valve) pneumatically connected (e.g., by a crimp or swage) to a first end 72 of the strand 58 and a one-way outlet valve/regulator 66 pneumatically connected (e.g., by a crimp or swage) to a second end 74 of the pressure vessel 40. The inlet valve 70 includes a mechanism permitting fluid to be transferred from a pressurized fluid fill source into the pressure vessel 40 through inlet valve 70 and to prevent fluid within the pressure vessel 40 from escaping through the inlet valve 70. The outlet valve/regulator 66 includes a well known mechanism permitting the outlet valve/regulator to be selectively configured to either prevent fluid within the pressure vessel 40 from escaping the vessel through the valve 66 or to permit fluid within the pressure vessel 40 to escape the vessel in a controlled manner through the valve 66. Preferably, the outlet valve/regulator 66 is operable to "step down" the pressure of fluid exiting the pressure vessel 40. For example, in typical medicinal applications of ambulatory oxygen, oxygen may be stored within the tank at up to 3,000 psi, and a regulator is provided to step down the outlet pressure to 20 to 50 psi. The outlet valve/regulator 66 may include a manually-operable control knob 68 for permitting manual control of a flow rate therefrom. A preferred inlet valve and a preferred outlet valve/regulator are described below.

A pressure relief valve (not shown) is preferably provided to accommodate internal pressure fluctuations due to thermal cycling or other causes.

Figure 6:
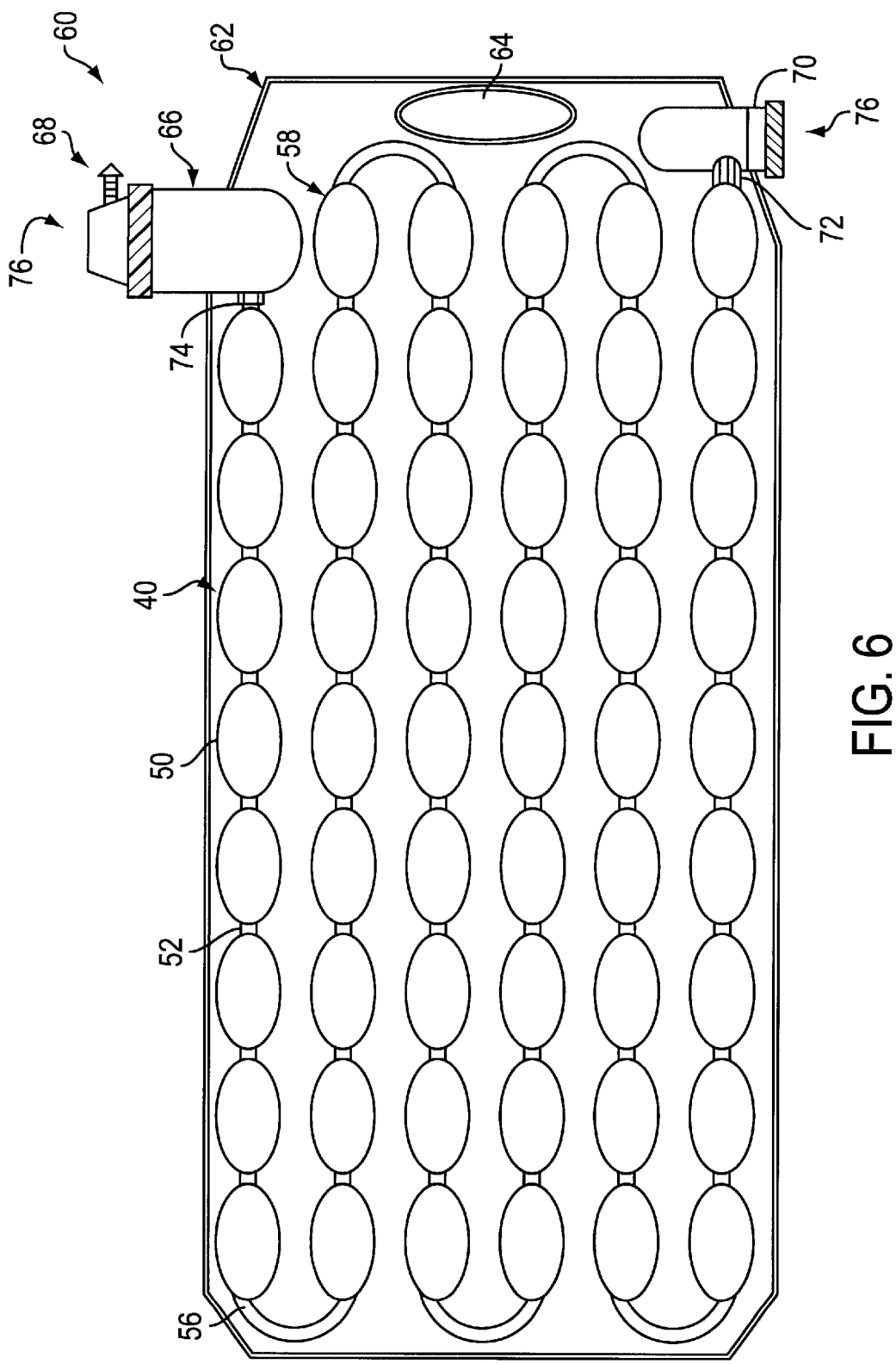
FIG. 6 is a portable pressurized fluid pack employing a container system according to the present invention.

In FIG. 6, the pressure vessel 40, inlet valve 70, and the outlet valve/regulator 66 are shown exposed on top of the housing 62. Preferably, the housing comprises dual halves of, for example, preformed foam shells that encase the pressure vessel 40. For the purposes of illustrating the structure of the embodiment of FIG. 6, however, a top half of the housing 62 is not shown. It should be understood, however, that a housing would substantially encase the pressure vessel 40 and at least portions of the outlet valve/regulator 66 and the inlet valve 70.

Figure 7:
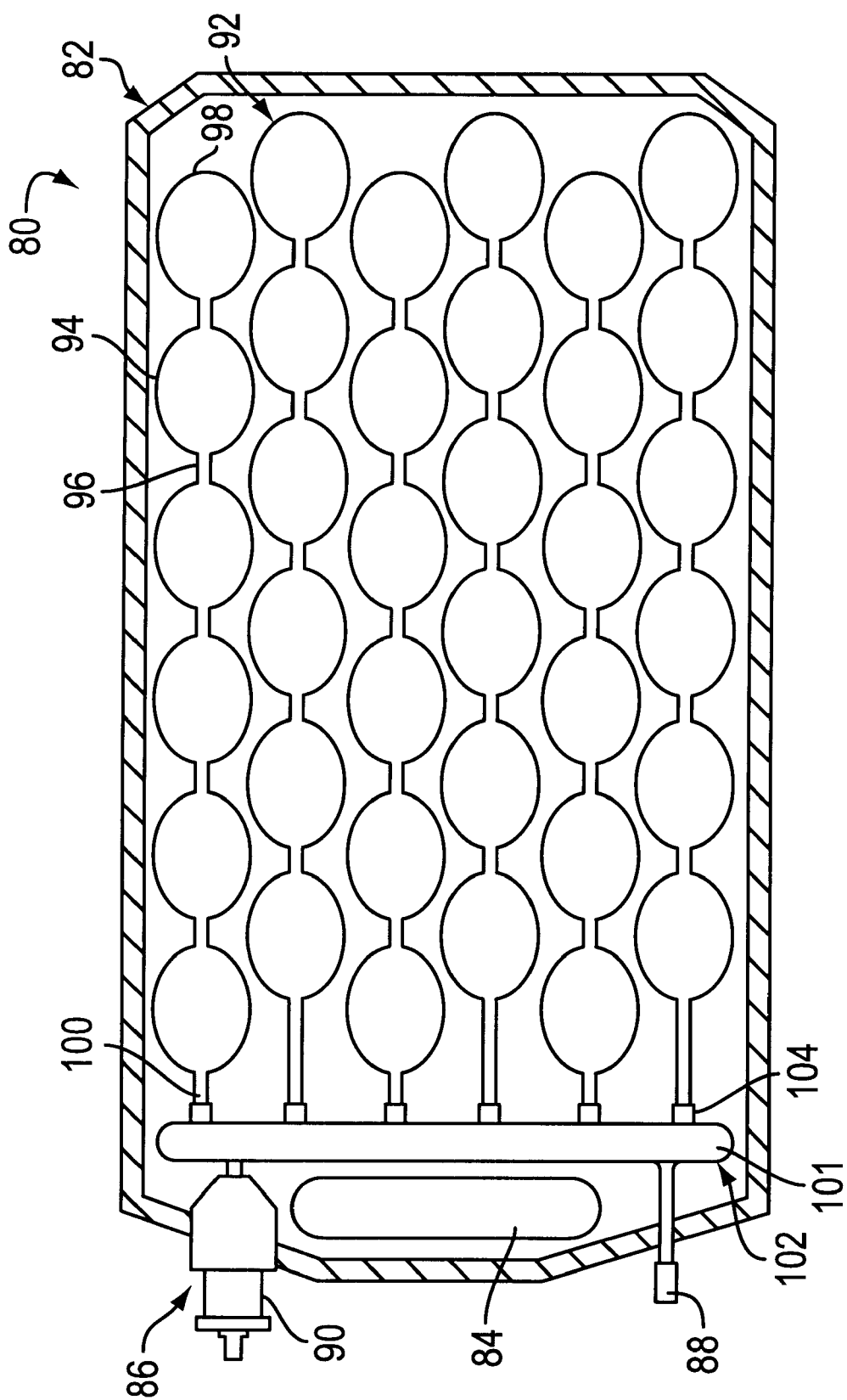
FIG. 7 is an alternate embodiment of a pressurized fluid pack employing the container system of the present invention.

FIG. 7 shows an alternate embodiment of a portable pressure pack generally designated by reference number 80. The pressure pack 80 includes a pressure vessel formed by a number of strands 92 of individual chambers 94 serially interconnected by interconnecting conduit sections 96 and arrange generally in parallel to each other. In the embodiment illustrated in FIG. 7, the pressure vessel includes six individual strands 92, but the pressure pack may include fewer than or more than six strands.

Each of the strands 92 has a first closed end 98 at the endmost of the chambers 94 of the strand 92 and an open terminal end 100 attached to a coupling structure defining an inner plenum, which, in the illustrated embodiment, comprises a distributor 102. The distributor 102 includes an elongated, generally hollow body 101 defining the inner plenum therein. Each of the strands 92 of interconnected chambers is pneumatically connected at its respective terminal end 100 by a connecting nipple 104 extending from the elongated body 101, so that each strand 92 of interconnected chambers 94 is in pneumatic communication with the inner plenum inside the distributor 102. Each strand 92 may be connected to the distributor 102 by a threaded interconnection, a crimp, or a swage, or any other suitable means for connecting a high pressure polymeric tube to a rigid fitting. A fluid transfer control system 86 is pneumatically connected to the distributor 102. In the illustrated embodiment, the fluid transfer control system 86 includes a one-way inlet valve 86 and a one-way outlet/regulator 90 pneumatically connected at generally opposite ends of the body 101 of the distributor 102.

The strands 92 of interconnected chambers 94, the distributor 102, and at least portions of the inlet valve 88 and the outlet valve/regulator 90 are encased within a housing 82, which may include a handle 84, as illustrated in FIG. 7, to facilitate carrying of the pressure pack 80.

Figure 8:
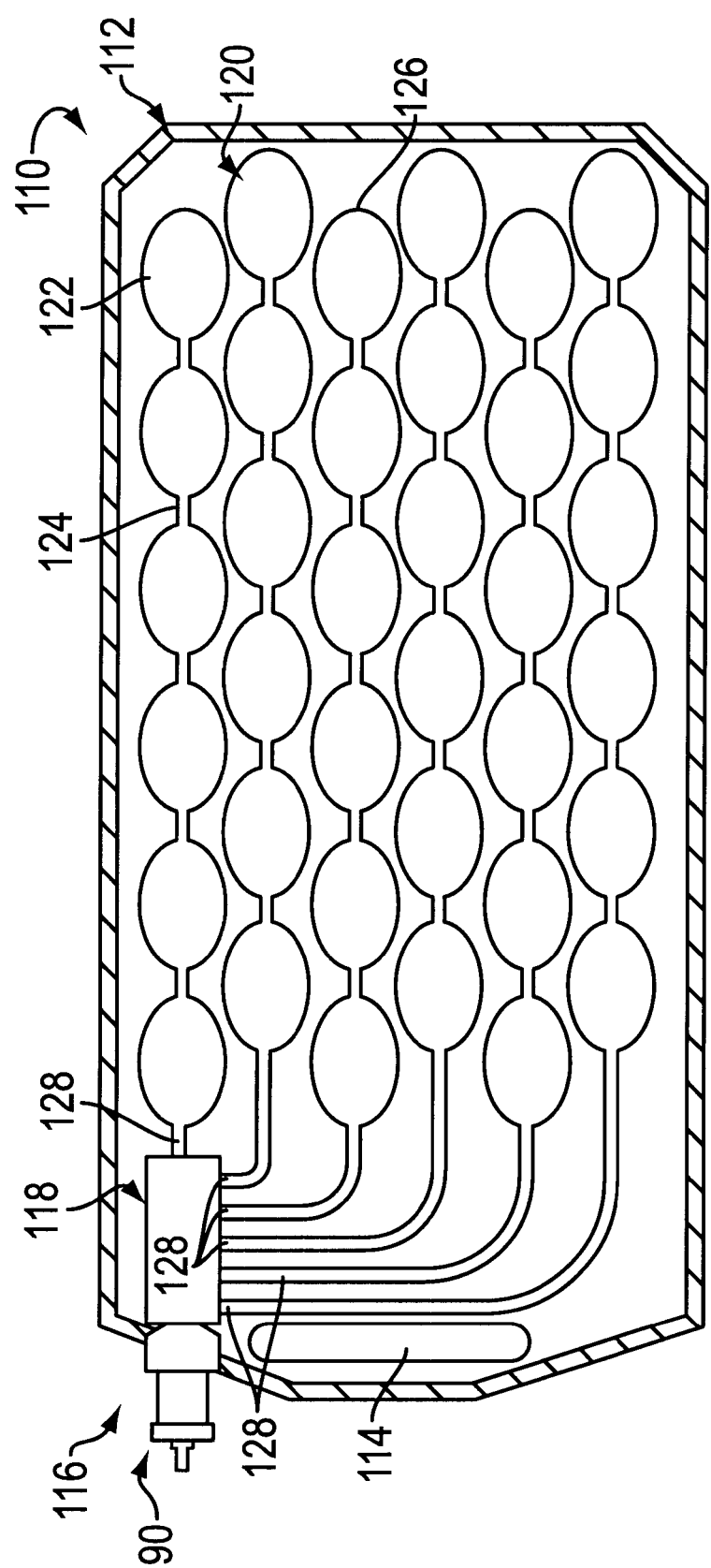
FIG. 8 is still another alternate embodiment of a pressurized fluid pack employing a container system according to the present invention.

In FIG. 8 is shown still another alternative embodiment of a pressure pack generally designated by reference number 110. The pressure pack 110 includes a pressure vessel 110. The pressure pack 110 includes a pressure vessel comprised of a number of generally parallel strands 120 of hollow chambers 122 serially interconnected by interconnecting conduit sections 124. Each of the strands 120 has a closed end 126 at the endmost of its chambers 122 and an open terminal end 128 attached to a coupling structure defining an inner plenum. In the illustrated embodiment, the coupling structure comprises a manifold 118 to which is pneumatically attached each of the respective terminal ends 128 of the strands 120. Each strand 120 may be connected to the manifold 118 by a threaded interconnection, a crimp, or a swage, or any other suitable means for connecting a high pressure polymeric tube to a rigid fitting. A fluid transfer control system 116 is attached to the manifold 118, and, in the illustrated embodiment, comprises a outlet valve/regulator 90 and an inlet valve (not shown).

The hollow chambers of the pressure vessels described above and shown in FIGS. 5A, 6, 7, and 8 can be of the type shown in FIGS. 2 and 2A having an internal perforated tubular core, or they can be of the type shown in FIG. 4 having no internal tubular core.

Figure 9:
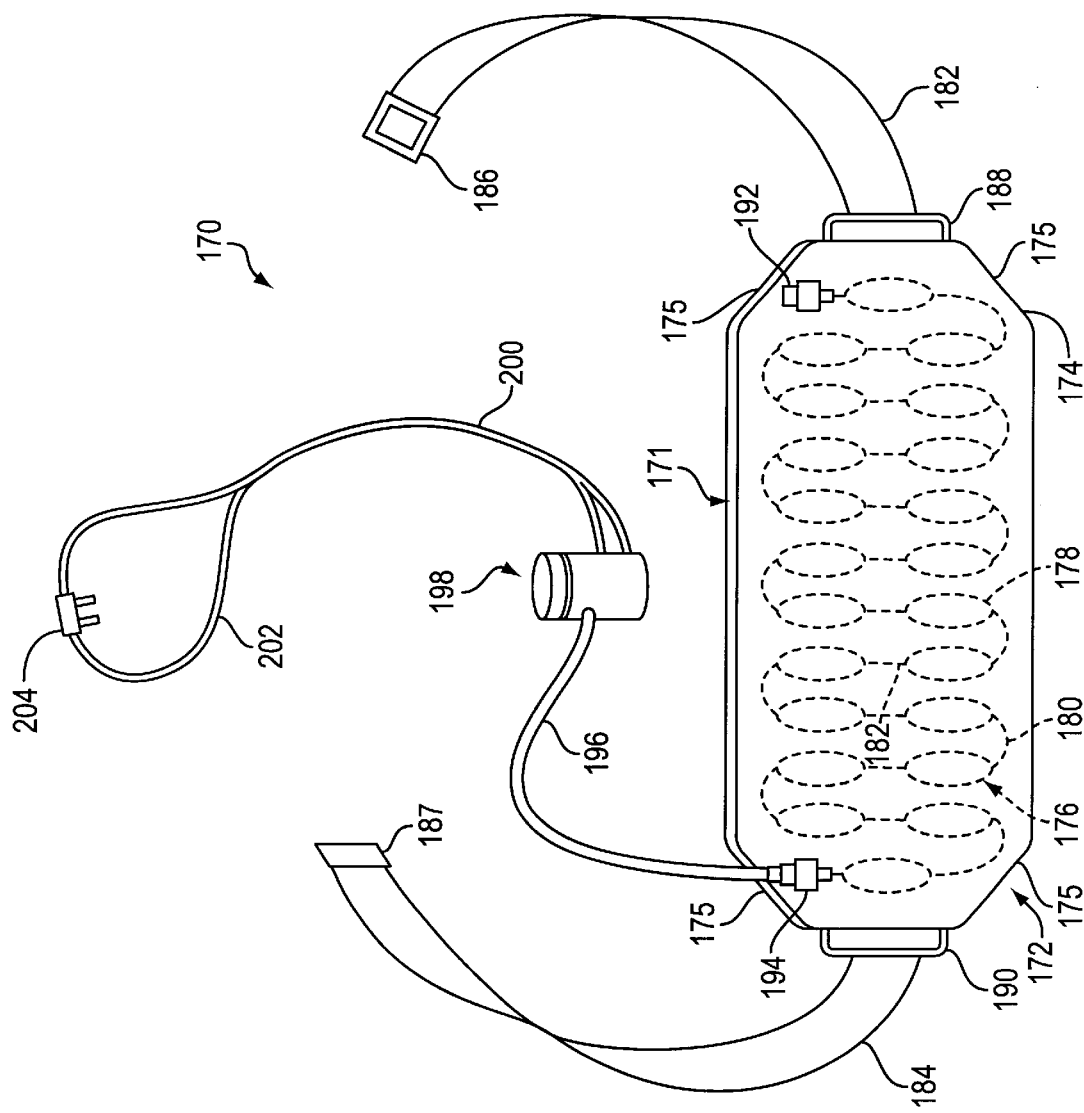
FIG. 9 is a perspective view of a wearable, portable oxygen delivery system incorporating a container system according to the present invention.

A pressure pack, such as any of those shown in FIGS. 6–8, is lightweight and compact, and therefore can be incorporated into a wearable carrier garment. A preferred configuration of a portable pressure pack incorporated into a wearable carrier garment is shown in FIG. 9. A wearable gas supply system 170 includes a pressure vessel 176 carried in a garment that takes the form of a cummerbund-style belt. The belt 172 includes a pressure vessel 176 having a plurality of interconnected chambers 178 serially interconnected by short straight conduit sections 182 and long bent conduit sections 180. The pressure vessel 176 can be of the type shown in FIGS. 1, 2, and 2A, having an internal, perforated tubular core, or the type shown in FIG. 4 having no internal tubular core. The chambers 178 are of a polymeric, filament winding-reinforced construction, as described above, and are preferably ellipsoidal, but may be spherical.

The pressure vessel 176 is encased in a padded housing 174 formed of a suitable padding material, such as neoprene. The housing 174 may comprise anterior and posterior cushioning layers secured to one another with a suitable adhesive with the pressure vessel and flow control system sandwiched in between. The anterior and posterior pads include recesses, or cavities, each conforming to one half of the chambers of the pressure vessel 176. A liquid impervious layer is preferably applied to the outer surface of the housing 174. Padded housing 174 preferably has angled corners 175 to facilitate the comfort for the wearer by avoiding possible sharp jabs that might be inflicted by a more pointed corner. In a preferred arrangement, the chambers 178 of the pressure vessel 176 are elongated ellipsoidal chambers and are arranged in a generally vertical, mutually parallel arrangement as shown by hidden lines so that the pressure vessel 176 and padded housing 174 are flexible about an axis extending vertically through the housing 174. Accordingly, the housing 174 can be generally conformed around the torso of a person wearing the belt 172.

Belt straps 182 and 184 are attached to the padded housing 174 by means of attaching brackets 188 and 190, respectively. Belt straps 182, 184 may comprise nylon web straps and preferably have adjustable lengths. Attaching brackets 188, 190 may be adhesively secured between the opposed layers of padding forming the padded housing 174. Alternatively, straps 182 and 184 could be provided as one continuous strap extending completely across the padded housing 174, and attaching brackets 188 190. Such a design has certain advantages in that it eliminates tensile forces at the attaching brackets 188 and 190 that can separate the brackets from the housing 174. Strap 182 can include a buckle 186 of conventional design that attaches to an end 187 of the other strap 184.

A one-way inlet valve 192 is connected to one end of the pressure vessel 176, and a one-way outlet valve/regulator 194 is connected to the opposite end of the pressure vessel 176. Both the inlet valve 192 and the outlet valve 194 are vertically oriented and are disposed on an outer face of the housing 174 and positioned so that the respective tops thereof do not project above a top edge 171 of the housing 174 and most preferably do not project above the adjacent angled corners 175. By having the inlet valve 192 and the outlet valve 194 oriented vertically and positioned on the front face of the housing 174 and recessed below a top edge thereof, there is less likelihood that the person wearing the belt 172 will experience discomfort from being jabbed by either of the valves 192 or 194.

A gas delivery mechanism is pneumatically connected to the fluid transfer control system for delivering metered fluid from the pressure vessel to a person. In the illustrated embodiment, an oxygen delivery system is connected to the outlet valve 194. More particularly, in the illustrated embodiment, a flexible tube 196 connects the outlet valve/ regulator 194 to a flow control valve 198. Flow control valve 198 is preferably a pneumatic demand oxygen conservor valve or an electronic oxygen conservor valve. Pneumatic demand oxygen conservor valves are constructed and arranged to dispense a pre-defined volume of low pressure oxygen (referred to as a "bolus" of oxygen) to a patient in response to inhalation by the patient and to otherwise suspend oxygen flow from the pressure vessel during noninhaling episodes of the patient's breathing cycle. Pneumatic demand oxygen conservor valves are described in U.S. Pat. No. 5,360,000 and in PCT Publication No. WO 97/11734A1, the respective disclosures of which are hereby incorporated by reference. A most preferred pneumatic demand oxygen conservor of the type that can be clipped onto the belt of a person receiving the supplemental oxygen is disclosed in U.S. patent application Ser. No. 09/435,174 filed Nov. 5, 1999, the disclosure of which is hereby incorporated by reference.

A dual lumen flexible tube 200 extends from the flow control valve 198 toward a loop 202 formed by the two lumen of the tube 200, the respective ends of which connect to a gas delivery mechanism, such as a dual lumen nasal cannula 204. A dual lumen nasal cannula communicates the patient's breathing status through one of the lumen of the dual lumen tube 200 to the flow control valve 198 and delivers oxygen to the patient during inhalation through the other lumen of the dual lumen tube 200. A suitable dual lumen nasal cannula is described in U.S. Pat. No. 4,989,599, the disclosure of which is hereby incorporated by reference.

Accordingly, it can be appreciated that the cummerbund-style belt 172 shown in FIG. 9 can provide a lightweight, unobtrusive, portable supply of pressurized fluid, such as oxygen, and can be worn around the lower torso of the person receiving the fluid with the padded housing 174 in front of the user against his or her abdomen or behind the user against his or her lower back.

Figure 10:
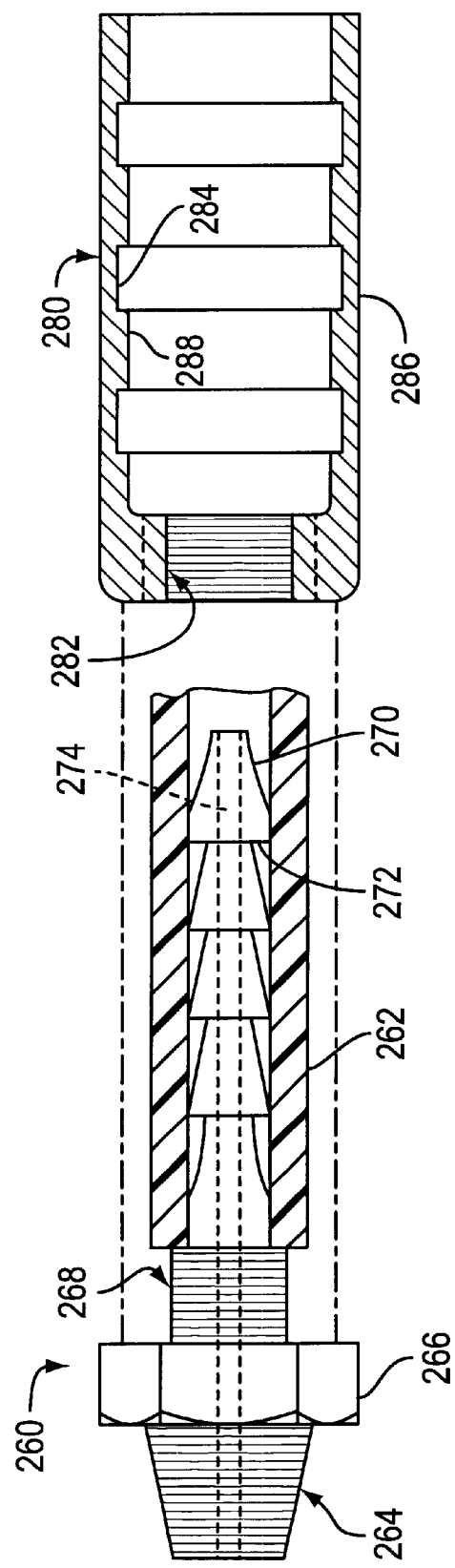
FIG. 10 is a partial, exploded view in longitudinal section of a system for securing a polymeric tube to a mechanical fitting.

FIG. 10 shows a preferred arrangement for attaching a mechanical fitting 260 to a polymeric tube 262 in a manner that can withstand high pressures within the tube 262. Such fittings 260 can be attached to the ends of a continuous strand of serially connected hollow chambers for connecting inlet and outlet valves at the opposite ends. For example, fittings 34 and 36 shown in FIG. 1 could be attached in the manner to be described. The mechanical fitting 260 has a body portion, which, in the illustrated embodiment includes a threaded end 264 to which can be attached another component, such as a valve or a gauge, and a faceted portion 266 that can be engaged by a tool such as a wrench. End 264 is shown as an exteriorly threaded male connector portion, but could be an interiorly threaded female connector portion. An exteriorly threaded collar 268 extends to the right of the faceted portion 266. An inserting projection 270 extends from the threaded collar 268 and has formed thereon a series of barbs 272 of the "Christmas tree" or corrugated type that, due to the angle of each of the barbs 272, permits the projection 270 to be inserted into the polymeric tube 262, as shown, but resists removal of the projection 270 from the polymeric tube 262. A channel 274 extends through the entire mechanical fitting 260 to permit fluid transfer communication through the fitting 260 into a pressure vessel.

A connecting ferrule 280 has a generally hollow, cylindrical shape and has an interiorly threaded opening 282 formed at one end thereof. The remainder of the ferrule extending to the right of the threaded opening 282 is a crimping portion 286. Ferrule 280 is preferably made from 6061 T6 aluminum. The crimping portion 286 has internally-formed ridges 288 and grooves 284. The inside diameter of the ridges 288 in an uncrimped ferrule 280 is preferably greater than the outside diameter of the polymeric tube 262 to permit the uncrimped ferrule to be installed over the tube 262.

Attachment of the fitting 260 to the tube 262 is affected by first screwing the threaded collar 268 into the threaded opening 282 of the ferrule 280. Alternatively, the ferrule 280 can be connected to the fitting 260 by other means. For example, the ferrule 280 may be secured to the fitting 260 by a twist and lock arrangement or by welding (or soldering or brazing) the ferrule 280 to the fitting 260. The polymeric tube 262 is then inserted over the inserting projection 270 and into a space between the crimping portion 286 and the inserting projection 270. The crimping portion 286 is then crimped, or swaged, radially inwardly in a known manner to thereby urge the barbs 272 and the ridges 288 and grooves 284 into locking deforming engagement with the tube 262. Accordingly, the tube 262 is securely held to the fitting 260 by both the frictional engagement of the tube 262 with the barbs 272 of the inserting projection 270 as well as the frictional engagement of the tube 262 with the grooves 284 and ridges 288 of the ferrule 280, which itself is secured to the fitting 260, e.g., by threaded engagement of the threaded collar 268 with the threaded opening 282.

A connecting arrangement of the type shown in FIG. 10 could also be used, for example, for attaching the strands 92 of interconnected chambers to the connecting nipples 104 of the distributor 102 in FIG. 7 or to attach the strands of interconnected chambers 120 to the connecting nipples 138 and 140 of the manifold 118 of FIG. 8.

Figure 11A:
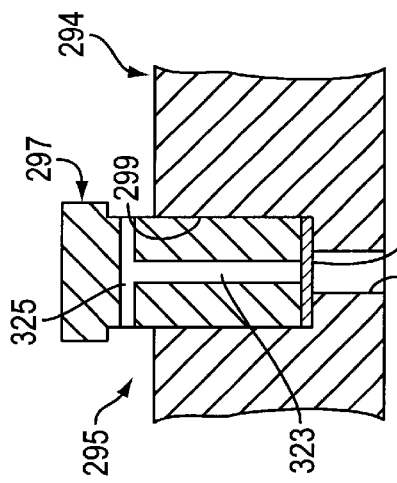
FIG. 11A is an enlarged view of a portion of FIG. 11 within circle "A".
Figure 11:
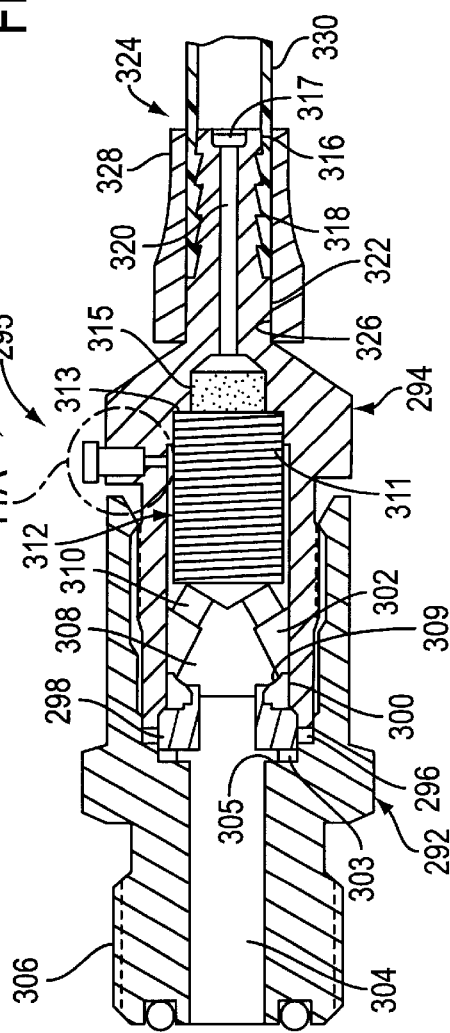
FIG. 11 is a partial view in longitudinal section of a preferred inlet valve for incorporation into the pressure pack employing the container system of the present invention.

FIG. 11 shows a preferred embodiment of an inlet valve 290. The valve 290 is a modified version of a poppet style inlet valve of the type generally described in U.S. Pat. No. 4,665,943, the disclosure of which is hereby incorporated by reference. The inlet valve 290 includes an inlet body 292 to which is attached an outlet body 294. An inlet gasket 296 is axially disposed between the inlet body 292 and the outlet body 294. The outlet body 294 has formed therein an inner valve chamber 302. An annular sealing insert 298 is disposed in the inner valve chamber 302 and engages a gasket 303 that bears against a shoulder 305 formed interiorly of the inlet body 292. An inlet channel 304 formed in the inlet body 292 communicates with the inner valve chamber 302. The inlet body 292 may have formed thereon exterior threads 306 for attaching thereto a fluid filling device.

A poppet valve body 308 is slidably disposed within the inner valve chamber 302. At one end of the poppet valve body is an annular sealing shoulder 309 that, when the valve body 308 is in a closed position as shown in FIG. 11, engages the annular sealing insert 298 and an O-ring seal 300. The poppet valve body 308 is a body of revolution having a generally frustoconical shape. At an end of the body 308 opposite the annular sealing shoulder 309, a plurality of legs 310 extend radially outwardly toward the inner walls defining the inner valve chamber 302. A coil spring 312 bears against an annular shoulder 313 formed in a spring seat 311 formed in the outlet body 294. The spring 312 extends into the inner valve chamber 302 and bears against the legs 310 of the poppet valve body 308, thereby urging the annular sealing shoulder 309 into closing engagement with the annular sealing insert 298 and the O-ring seal 300. A chamber 315 is formed inside the outlet body 294 to the immediate right of the spring 312. An outlet channel 320 extends from the chamber 315 through an exteriorly threaded collar 322 and an inserting projection 316. A sintered brass filter element 314 can be disposed in the chamber 315 in line with outlet channel 320 to filter fluid passing through the inlet valve 290. Alternatively, or in addition, a filter element 317 (e.g., a sintered brass element), can be provided at a position along the outlet channel 320, such as at its terminal end, as shown.

A polymeric tube 330 can be attached to the inlet valve 290 by the connecting arrangement described above and shown in FIG. 10. That is, outwardly projecting barbs 318 are formed on the exterior of the inserting portion 316, which is inserted into the tube 330. A ferrule 324 having an interiorly threaded opening 326 and a crimping portion 328 is threaded onto the exteriorly threaded collar 322 of the outlet body 294. The crimping portion 328 is then crimped, as shown, onto the tube 330 to pinch the tube 330 into frictional, locking engagement with the barbs 318 of the inserting projection 316.

The inlet valve 290 is shown in FIG. 11 in a closed configuration. In the closed configuration, the annular sealing shoulder 309 of the poppet valve body 308 is engaged with the annular sealing insert 298 and the O-ring seal 300. Upon application of a pressurized fluid into the inlet channel 304 sufficient to overcome the spring force of the spring 312, the poppet valve body 308 is urged to the right, thereby creating a gap between the sealing shoulder 309 and the sealing insert 298 and O-ring 300. The pressurized fluid can then pass through this gap, around the poppet valve body 308, through the spaces between adjacent ones of the radial legs 310, through the open center portion of the spring 312, through the filter 314, and through the outlet channel 320 into the polymeric tube 330 of the pressure vessel. When the source of pressurized fluid is removed from the inlet body 292, the force of the spring 312, as well as the force of the pressurized fluid within the pressure vessel, urge the poppet valve body 308 to the left so that the annular sealing shoulder 309 is again in sealing contact with both the annular sealing insert 298 and the O-ring seal 300, to thereby prevent pressurized fluid from exiting the pressure vessel through the inlet valve 290.

The inlet valve 290 is preferably configured to be coupled to any of several industry standard high-pressure fill valves. It is known that adiabatic compression caused by filling a pressure vessel too rapidly can cause excessive temperatures within the pressure vessel near the fill valve. Such a rapid filling technique is recognized as hazardous to all existing high-pressure vessels, and procedures discouraging such a practice are known. Many fill valves, however, are manually operated and thereby permit, either through carelessness, mistake, or inattention, an operator to open a fill valve completely and allow such an immediate and instantaneous pressurization in the filled tank to occur. Current high-pressure cylinders, typically made of a metal can withstand such an improper fill technique, although such cylinders can get dangerously hot when filled in such a manner. Pressure vessels according to the present invention are constructed of polymeric materials which can auto-ignite at about 400° F. in the presence of pure oxygen. Calculations have demonstrated that the temperature at the closed end of a pressure vessel constructed in accordance with the present invention can exceed 1700° F. during a rapid filling pressurization.

Accordingly, as a safety measure that may prevent auto-ignition of the polymeric pressure vessel due to an improper rapid filling procedure, the outlet channel 320 of the inlet valve 290 is made restrictively narrow so that the outlet channel 320 functions as a regulator to step down the pressure of fluid flowing into the pressure vessel from a fill valve. In accordance with aspects of the present invention, it is preferred that the outlet channel 320 in the inlet valve 290 be of a size that is so restrictive as to prevent the internal pressure within the pressure vessel from exceeding 500 psig five seconds into a fill procedure where the inlet valve 290 is instantaneously exposed to a 2,000 psig fill source. The outlet channel 320 must, however, be large enough to allow proper filling of the pressure vessel when a correct filling technique is followed. The presently preferred diameter of the outlet channel 320 is 0.003–0.010 inches in diameter.

A sintered brass filter element 314 (and/or filter element 317), if employed in the inlet valve 290, also functions as a restriction in the flow path and can assist in stepping down the fill pressure.

The inlet valve 290 may include a pressure relief mechanism, such as rupture disk assembly 295, constructed and arranged to relieve excessive pressure buildup in the inner valve chamber 302 which communicates pneumatically with the interior of the pressure vessel. As shown in FIG. 11A, the rupture disk assembly 295 includes a disk-retaining pin 297 inserted into a pin-receiving opening 299 formed in the side wall of the outlet body 294 of the inlet valve 290. Pin 297 and opening 299 may each be threaded. A pilot hole 319 extends from the pin-receiving opening 299 into the inner valve chamber 302. A rupture disk 321 is positioned in the bottom of the pin-receiving opening 299 and is formed of a soft, rupturable material, such as copper. An axial channel 323 is formed in the pin 297. Axial channel 323 connects to a transverse radial channel 325 formed through the pin 297. The rupture disk 321 is constructed and arranged to rupture when the pressure in the inner valve chamber 302 exceeds a predefined maximum threshold pressure, thereby permitting pressure relief through the pilot hole 319 and the channels 323 and 325.

Figure 12:
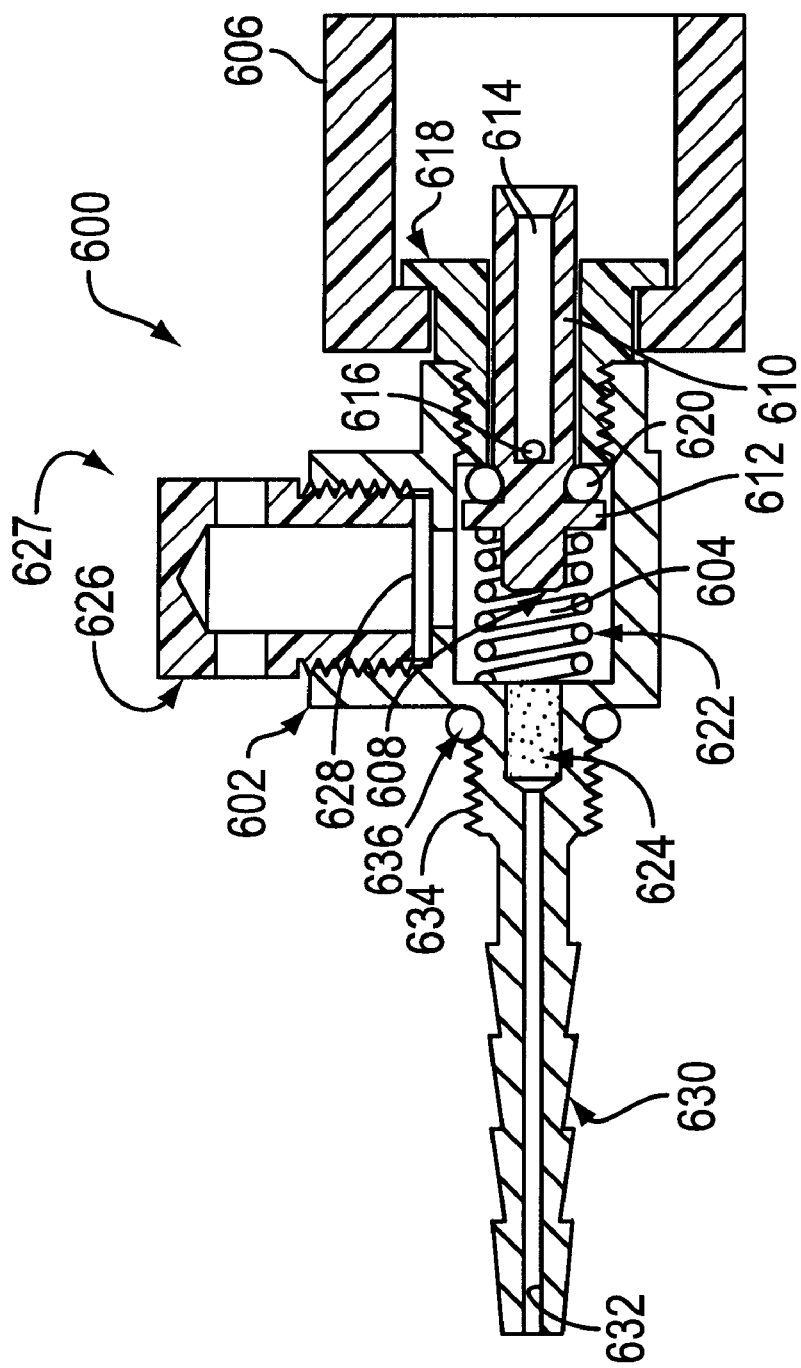
FIG. 12 is partial view in longitudinal section of an alternative inlet valve for incorporation into the pressure pack employing the container system of the present invention.

An alternative one-way inlet valve is designated generally by reference number 600 in FIG. 12. The inlet valve 600 is a one-way valve of the type commonly known as a pin valve. The valve 600 includes a valve body 602 having defined therein an inner chamber 604. A swivel fitting 606 is coupled to the valve body 602 by means of a radial flange of a threaded pin-retaining screw 618 threaded into the valve body 602. A flow control pin 608 is disposed inside the inner chamber 604 of the valve body 602. A shaft 610 of the pin 608 extends through and is guided by an axial bore formed through the pin-retaining screw 618. A radial flange 612 projects from the shaft 610 of the pin 608. An axial bore 614 extends from one end of the shaft 610, and a radial through hole 616 extends through the shaft 610 in communication with the axial bore 614. A spring 622 engages the radial flange 612 of the pin 608 and urges the pin 608 into engagement with the axial end of the pin-retaining screw 618, with an O-ring 620 disposed between the flange 612 of the pin 608 and the pin-retaining screw 618. With the pin 608 urged against the pin-retaining screw 618, airflow between the swivel fitting 606 and the inner valve chamber 604 is prevented.

The inlet valve 600 preferably includes a pressure relief mechanism, such as a rupture disk assembly 627. The rupture disk assembly 627 includes a rupture disk retainer 626 threaded into the valve body 602 and a rupture disk 628 formed from a rupturable material, such as copper. When pressure within the inner chamber 604 exceeds a predetermined threshold value at which the rupture disk 628 will rupture, pressure is released from the chamber 604 through axial and radial channels formed in the rupture disk retainer 626.

A barbed projection 630 extends from the valve body 602. The barbed projection 630 includes barbs which partially penetrate and engage a polymeric tube into which the projection 630 is inserted. A threaded collar 634 is formed at the base of the barbed projection 630 and is engaged by a ferrule (not shown, see, e.g., ferrule 280 in FIG. 10 and accompanying disclosure) having a threaded opening at one end thereof and a crimping portion to be crimped onto the polymeric tube to thereby secure the tube to the barbed projection 630. An external O-ring 636 may be provided at the base of the threaded collar 634 to provide additional sealing between the valve body 602 and a ferrule (not shown) threaded onto the threaded collar 634.

An outlet channel 632 extends through the barbed projection 630. The outlet channel 632 may be made restrictively narrow, such as outlet channel 320 of inlet valve 290 shown in FIG. 11, so that the outlet channel 632 functions as a regulator to step down the pressure of fluid flowing into the pressure vessel from a fill valve, as described above. A filter element 624, for example a sintered brass filter element, can be disposed at the mouth of the outlet channel 632.

When an appropriate fill fitting is coupled to the swivel fitting 606, the fill fitting includes a structure or mechanism, as is well known in the art, that engages the pin 608 to urge the pin against the force of spring 22 out of engagement with the spring-retaining screw 618. Thereafter, pressurized fluid introduced at the swivel fitting 606 passes into the axial bore 614 and escapes the axial bore 614 through the radial hole 616 and flows into the inner chamber 604, and through the filter 624 and the outlet channel 632. When the fill fitting is removed from the swivel fitting 606, the pin 608, under the force generated by the spring 622, moves back into engagement with the pin-retaining screw 618 to thereby prevent the flow of fluid out of the inner chamber 604.

FIG. 13 shows a preferred embodiment of an outlet valve/regulator assembly 370. The assembly 370 includes an outlet valve 372 attached to a polymeric tubing 410 by means of a ferrule 402.

The outlet valve 372 has a high-pressure end 374 with a high-pressure barbed projection 408 and a threaded collar portion 404. A low pressure end 376 has a barbed low-pressure outlet projection 400 or some other structure for pneumatically connecting the outlet valve assembly 372 to a fluid delivery system. An internal chamber 378 is defied between the high-pressure end 374 and the low-pressure end 376. A regulator seat 380 is disposed within the internal chamber 378 at the terminal end of passage 411 extending through barbed projection 408. For clarity, the remaining internal pressure-reducing components normally disposed within the internal chamber 378, and well-known to those skilled in the art, are not shown.

The outlet valve 372 may include a pressure relief mechanism, such as rupture disk assembly 382, constructed and arranged to relieve excessive pressure buildup in the high-pressure side of the internal chamber 378. As shown in FIG. 13A, the rupture disk assembly 382 includes a disk-retaining pin 388 inserted into a pin-receiving opening 390 formed in the side wall of the high-pressure end 374 of the outlet valve 372. Pin 388 and opening 390 may each be threaded. A pilot hole 384 extends from the pin-receiving opening 390 into the high-pressure side of the internal chamber 378. A rupture disk 386 is positioned in the bottom of the pin-receiving opening 390 and is formed of a soft, rupturable material, such as copper. An axial channel 392 is formed in the pin 388. Axial channel 392 connects to a transverse radial channel 394 formed through the pin 388. The rupture disk 386 is constructed and arranged to rupture when the pressure in the high-pressure side of the internal chamber 378 exceeds a predefined maximum threshold pressure, thereby permitting pressure relief through the pilot hole 384 and the channels 392 and 394.

Ferrule 402 includes a threaded opening 406 that threadedly engages the threaded collar 404 of the high-pressure end 374. Ferrule 402 further includes a crimping portion 412 that may be crimped (as shown) onto the polymeric tubing 410 to secure the tubing 410 onto the barbed projection 408.

While the invention has been described in connection with what are presently considered to be the most practical and preferred embodiments, it is to be understood that the invention is not to be limited to the disclosed embodiments, but, on the contrary, it is intended to cover various modifications and equivalent arrangements included within the spirit and scope of the appended claims. Thus, it is to be understood that variations in the particular parameters used in defining the present invention can be made without departing from the novel aspects of this invention as defined in the following claims.

What is claimed is:

1. A container system for pressurized fluids comprising:
   a pressure vessel comprising a plurality of hollow chambers formed from a polymeric material interconnected by polymeric conduit sections disposed between consecutive ones of said hollow chambers;
   a fluid transfer control valve attached to said pressure vessel and constructed and arranged to control flow of fluid with respect to an interior of said pressure vessel defined by the interiors of said hollow chambers and said conduit sections, said fluid transfer control valve comprising:
   a valve body having a threaded collar and a fluid chamber formed therein, at least a portion of said chamber being in fluid communication with the interior of said pressure vessel;

a pressure relief mechanism coupled to said fluid chamber and constructed and arranged to permit fluid to flow out of said pressure vessel when the fluid within said pressure vessel exceeds a prescribed threshold level to thereby reduce pressure within said pressure vessel; and a projection extending from said valve body adjacent said threaded collar to be inserted into a conduit section of said pressure vessel, said projection having barbs formed thereon constructed and arranged to permit said projection to be inserted into the conduit section but to resist removal of said projection from the conduit section, said valve body having a fluid flow path extending from said chamber through said projection; and a ferrule for securing said conduit section onto said projection, said ferrule having a threaded opening at one longitudinal end thereof which is threadedly engaged with said threaded collar of said valve body to connect said ferrule to said valve body, said ferrule being arranged in an outwardly spaced coaxial relation with respect to said projection, said ferrule having a crimping portion constructed and arranged to be radially crimped onto a portion of the conduit section into which said projection is inserted to thereby compress the portion of the conduit section into said barbs and secure the conduit section onto said projection.

2. The container system of claim 1, wherein said pressure relief mechanism comprises a rupture disk assembly, said rupture disk assembly comprising:

a rupture disk positioned with respect to said valve body so as to be exposed to fluid pressure within said fluid chamber; and a disk retainer securing said rupture disk with respect to said valve body, said retainer having fluid flow channels formed therein, wherein fluid flow from said fluid chamber through said channels is blocked by said rupture disk, wherein said rupture disk is constructed and arranged to rupture when fluid pressure within said fluid chamber exceeds the prescribed threshold level to thereby permit fluid to flow from said fluid chamber through said fluid flow channels formed in said disk retainer.

3. The container system of claim 1, wherein said pressure vessel comprises one continuous strand of interconnected ones of said plurality of chambers spaced apart by ones of said conduit sections, said continuous strand being arranged in a sinuous configuration turned alternately back and forth upon itself with successive extents of said strand being generally parallel to each other, said fluid transfer control valve being attached to said pressure vessel at one end of said continuous strand.

4. The container system of claim 1, wherein said pressure vessel further comprises:

two or more continuous strands of interconnected ones of said plurality of hollow chambers spaced apart by ones of said conduit sections, portions of said two or more continuous strands being arranged generally parallel to each other; and a coupling structure defining an inner plenum, wherein a first end of each of said two or more continuous strands is pneumatically sealed and a second end of each of said two or more continuous strands is connected to said coupling structure in pneumatic communication with said inner plenum and wherein said fluid transfer control valve is attached to said coupling structure.

5. The container system of claim 4, wherein said coupling structure comprises a distributor having an elongated shape and being arranged transversely to the parallel portions of said two or more strands, each of said two or more strands being connected to said distributor at a different position along the length thereof.

6. The container system of claim 4, wherein said coupling structure comprises a manifold, each of said two or more strands being connected to said manifold.

7. The container system of claim 1, further comprising an inner tubular core extending through each of said plurality of chambers in generally coaxial alignment with said conduit sections, each inner tubular core having formed therein at least one aperture disposed within the interior of each of said chambers.

8. The container system of claim 1, wherein said fluid transfer control valve comprises a one-way inlet valve attached to said pressure vessel, said one-way inlet valve being constructed and arranged to permit fluid under pressure to be transferred through said inlet valve and into said pressure vessel and to prevent fluid within said pressure vessel from escaping therefrom through said inlet valve.

9. The container system of claim 8, wherein said valve body of said inlet valve has a fluid flow channel formed therein through which fluid flows from an external source of pressurized fluid into said pressure vessel, and wherein said inlet valve further comprises a filter element disposed along said fluid flow channel to filter fluid flowing through said fluid flow path into said pressure vessel.

10. The container system of claim 8, wherein said valve body of said inlet valve has a fluid flow channel formed therein through which fluid flows from an external source of pressurized fluid into said pressure vessel, and wherein at least a portion of said fluid flow channel comprises a restrictive flow path constructed and arranged to reduce the pressure of fluid flowing from the external source of pressurized fluid into said pressure vessel.

11. The container system of claim 10, wherein said restrictive flow path is of a size that is so restrictive as to prevent the internal pressure within the pressure vessel from exceeding 500 psig five seconds into a fill procedure where the inlet valve is instantaneously exposed to a 2,000 psig fill source.

12. The container system of claim 11, wherein said restrictive flow path has a diameter between 0.003–0.010 inches.

13. The container system of claim 8, wherein said one-way inlet valve comprises a pressure actuatable poppet valve.

14. The container system of claim 8, wherein said one-way inlet valve comprises a mechanically actuatable pin valve.

15. The container system of claim 1, wherein said fluid transfer control valve comprises a regulator outlet valve attached to said pressure vessel, said regulator outlet valve being constructed and arranged to be selectively configured to either prevent fluid within said pressure vessel from escaping therefrom through said regulator outlet valve or to permit fluid within said pressure vessel to escape therefrom through said regulator outlet valve at an outlet pressure that deviates from a pressure of the fluid within said pressure vessel.

16. The container system of claim 1, wherein said hollow chambers of said pressure vessel have a generally spherical or ellipsoidal shape.

17. A container system for pressurized fluids comprising:

a pressure vessel comprising a plurality of hollow chambers formed from a polymeric material interconnected by polymeric conduit sections disposed between consecutive ones of said hollow chambers;

a fluid transfer control valve attached to said pressure vessel and constructed and arranged to control flow of fluid with respect to an interior of said pressure vessel defined by the interiors of said hollow chambers and said conduit sections, said fluid transfer control valve comprising:

a valve body having a threaded collar and a fluid flow channel formed therein through which fluid flows with respect to the interior of said pressure vessel;

a filter element disposed along said fluid flow channel to filter fluid flowing through said fluid flow path; and a projection extending from said valve body adjacent said threaded collar to be inserted into a conduit section of said pressure vessel, said projection having barbs formed thereon constructed and arranged to permit said projection to be inserted into the conduit section but to resist removal of said projection from the conduit section, said valve body having a fluid flow path extending from said chamber through said projection; and a ferrule for securing said conduit section onto said projection, said ferrule having a threaded opening at one longitudinal end thereof which is threadedly engaged with said threaded collar of said valve body to connect said ferrule to said valve body, said ferrule being arranged in an outwardly spaced coaxial relation with respect to said projection, said ferrule having a crimping portion constructed and arranged to be radially crimped onto a portion of the conduit section into which said projection is inserted to thereby compress the portion of the conduit section into said barbs and secure the conduit section onto said projection.

18. The container system of claim 17, wherein at least a portion of said fluid flow channel comprises a restrictive flow path constructed and arranged to reduce the pressure of fluid flowing from the external source of pressurized fluid into said pressure vessel.

19. The container system of claim 17, wherein said valve body has a fluid chamber formed therein, at least a portion of said chamber being in fluid communication with the interior of said pressure vessel, and wherein said fluid transfer control valve further includes a pressure relief mechanism coupled to said fluid chamber and constructed and arranged to permit fluid to flow out of said pressure vessel when the fluid within said pressure vessel exceeds a prescribed threshold level to thereby reduce pressure within said pressure vessel.

20. The container system of claim 19, wherein said pressure relief mechanism comprises a rupture disk assembly, said rupture disk assembly comprising:

a rupture disk positioned with respect to said valve body so as to be exposed to fluid pressure within said fluid chamber; and a disk retainer securing said rupture disk with respect to said valve body, said retainer having fluid flow channels formed therein, wherein fluid flow from said fluid chamber through said channels is blocked by said rupture disk, wherein said rupture disk is constructed and arranged to rupture when fluid pressure within said fluid chamber exceeds the prescribed threshold level to thereby permit fluid to flow from said fluid chamber through said fluid flow channels formed in said disk retainer.

21. A container system for pressurized fluids comprising:

a pressure vessel comprising:

two or more continuous strands of a plurality of hollow chambers formed from a polymeric material interconnected by polymeric conduit sections disposed between consecutive ones of said hollow chambers, portions of said two or more continuous strands being arranged generally parallel to each other; and a distributor having an elongated shape and defining an inner plenum, said distributor being arranged transversely to the parallel portions of said two or more continuous strands, wherein a first end of each of said two or more continuous strands is pneumatically sealed and a second end of each of said two or more continuous strands is connected to said distributor at a different position along the length thereof in pneumatic communication with said inner plenum; and a fluid transfer control valve attached to said distributor and constructed and arranged to control flow of fluid with respect to an interior of said pressure vessel defined by the interiors of said hollow chambers and said conduit sections, said fluid transfer control valve comprising:

a valve body having a fluid chamber formed therein, at least a portion of said chamber being in fluid communication with the interior of said pressure vessel; and a pressure relief mechanism coupled to said fluid chamber and constructed and arranged to permit fluid to flow out of said pressure vessel when the fluid within said pressure vessel exceeds a prescribed threshold level to thereby reduce pressure within said pressure vessel.

22. A container system for pressurized fluids comprising:

a pressure vessel comprising:

two or more continuous strands of a plurality of hollow chambers formed from a polymeric material interconnected by polymeric conduit sections disposed between consecutive ones of said hollow chambers, portions of said two or more continuous strands being arranged generally parallel to each other; and a manifold defining an inner plenum, wherein a first end of each of said two or more continuous strands is pneumatically sealed and a second end of each of said two or more continuous strands is connected to said manifold in pneumatic communication with said inner plenum; and a fluid transfer control valve attached to said manifold and constructed and arranged to control flow of fluid with respect to an interior of said pressure vessel defined by the interiors of said hollow chambers and said conduit sections, said fluid transfer control valve comprising:

a valve body having a fluid chamber formed therein, at least a portion of said chamber being in fluid communication with the interior of said pressure vessel; and a pressure relief mechanism coupled to said fluid chamber and constructed and arranged to permit fluid to flow out of said pressure vessel when the fluid within said pressure vessel exceeds a prescribed threshold level to thereby reduce pressure within said pressure vessel.

\* \* \* \* \*